United States Patent
Grafton et al.

[19]

[11] Patent Number: 6,056,778
[45] Date of Patent: May 2, 2000

[54] MENISCAL REPAIR DEVICE

[75] Inventors: R. Donald Grafton; Mark Brunsvold, both of Naples, Fla.

[73] Assignee: Arthrex, Inc., Naples, Fla.

[21] Appl. No.: 09/099,869

[22] Filed: Jun. 19, 1998

Related U.S. Application Data

[60] Provisional application No. 60/063,445, Oct. 29, 1997.

[51] Int. Cl.[7] .................................................. A61B 17/04
[52] U.S. Cl. .............................. 623/20; 606/77; 606/213; 606/220; 623/18
[58] Field of Search ......................... 623/20, 18; 606/77, 606/66, 67–72, 73, 74, 213, 220, 152; 24/456, 704.1, 706

[56] References Cited

U.S. PATENT DOCUMENTS

| | | | |
|---|---|---|---|
| 3,800,783 | 4/1974 | Jamshidi | 600/567 |
| 4,175,555 | 11/1979 | Herbert | 606/73 |
| 4,507,817 | 4/1985 | Staffeld | 7/158 |
| 4,532,926 | 8/1985 | O'Holla | 606/220 |
| 4,873,976 | 10/1989 | Schreiber | 606/213 |
| 4,884,572 | 12/1989 | Bays et al. | 606/139 |
| 4,895,148 | 1/1990 | Bays et al. | 606/213 |
| 4,924,865 | 5/1990 | Bays et al. | 606/77 |
| 4,976,715 | 12/1990 | Bays et al. | 606/77 |
| 5,059,206 | 10/1991 | Winters | 606/213 |
| 5,129,906 | 7/1992 | Ross et al. | 606/77 |
| 5,261,914 | 11/1993 | Warren | 606/73 |
| 5,342,376 | 8/1994 | Ruff | 606/151 |
| 5,364,400 | 11/1994 | Rego, Jr. et al. | 606/72 |
| 5,398,861 | 3/1995 | Green | 227/175 |
| 5,562,672 | 10/1996 | Huebner et al. | 606/73 |
| 5,569,252 | 10/1996 | Justin et al. | 606/73 |
| 5,723,008 | 3/1998 | Gordon | 623/13 |

FOREIGN PATENT DOCUMENTS

| | | |
|---|---|---|
| 0432320 | 6/1991 | European Pat. Off. . |
| 0513736 | 11/1992 | European Pat. Off. . |
| 0534152 | 3/1993 | European Pat. Off. . |

*Primary Examiner*—David H. Willse
*Assistant Examiner*—Suzette J. Jackson
*Attorney, Agent, or Firm*—Ostrolenk, Faber, Gerb & Soffen, LLP

[57] ABSTRACT

A meniscal tissue repair device includes an elongate body having a pointed distal tip. A plurality of lateral grooves is disposed along the body. Grooves disposed near the distal tip of the device are angled to open proximally and grooves disposed near the proximal end are angled to open distally. A torn meniscus can be repaired using the meniscal repair device by loading the meniscal repair device into an applicator, and inserting the barrel of the applicator through an incision in the knee at a location proximal and perpendicular to the tear in the meniscus. The applicator is actuated to drive the repair device distally into the meniscus across the tear. The distal travel of the repair device is limited by the distally-opening grooves of the repair device.

5 Claims, 2 Drawing Sheets

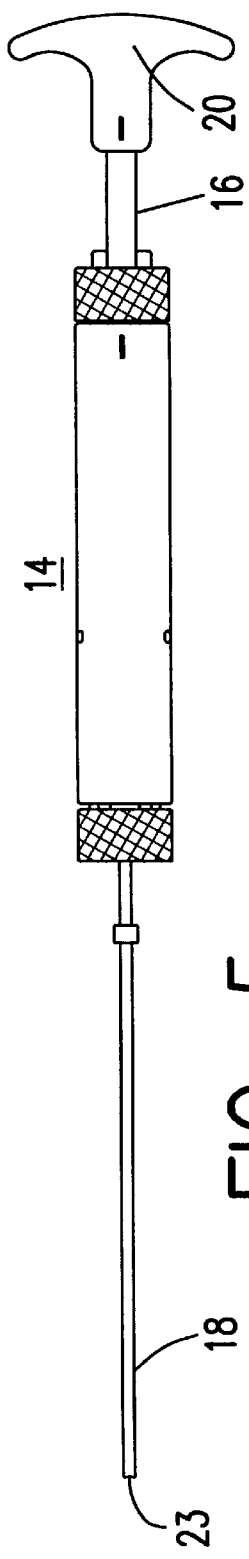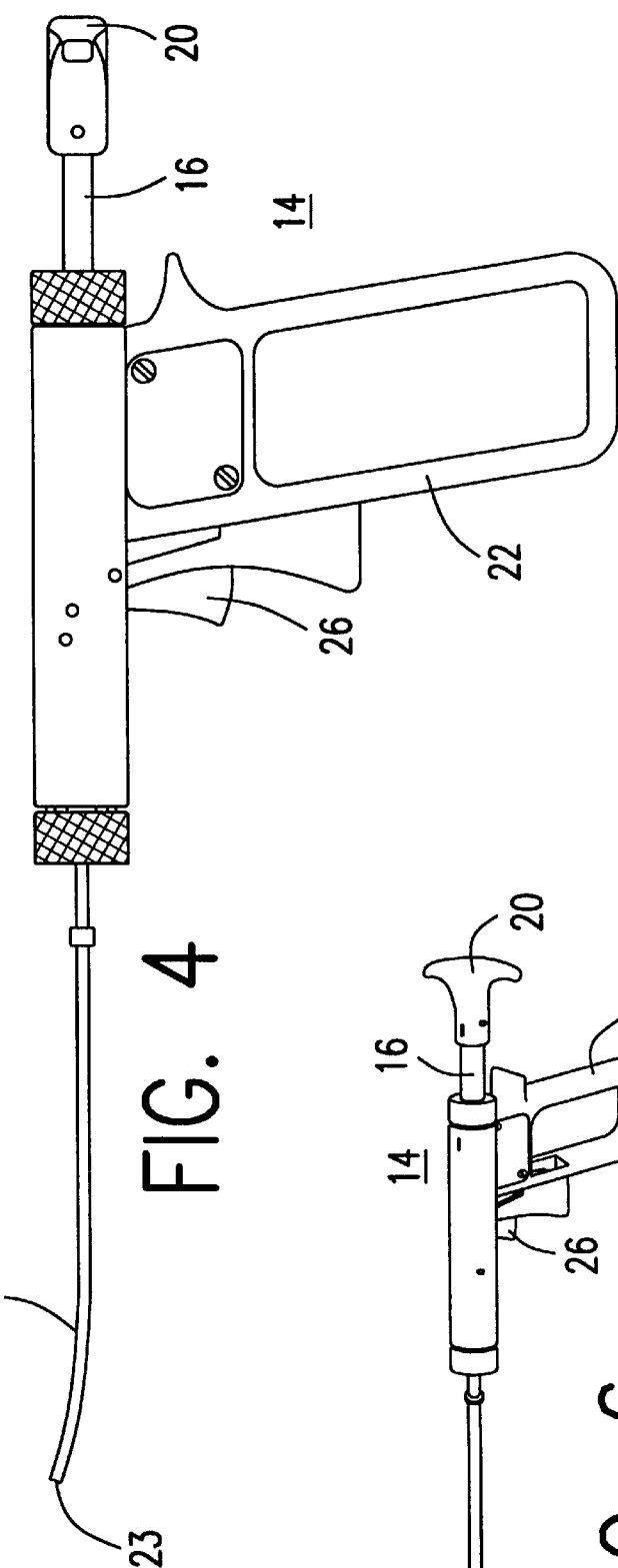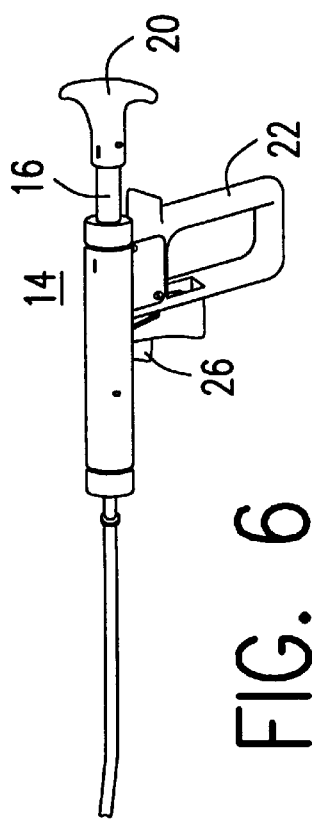

MENISCAL REPAIR DEVICE

This application claims the benefit of U.S. Provisional Application Ser. No. 60/063,445, filed Oct. 29, 1997, the entire disclosure of which is incorporated herein by reference.

BACKGROUND OF THE INVENTION

1. Field of the Invention

The present invention relates to surgical methods and apparatus for repair of meniscal tears.

2. Description of the Related Art

The menisci are crescent-shaped structures of fibrocartilaginous tissue located in the knee between the condyles of the tibia and the femur. The menisci, which are actually extensions of the tibia, serve to deepen the tibial plateau to better accommodate the opposing curvature of the articulating surface of the femoral condyle.

A typical injury to the knee is a meniscal tear, which can occur, for example, when the meniscus is displaced and caught between the femoral and tibial condyles during a sudden change of movement of the knee involving a combined flexion-rotation or extension-rotation motion. Meniscal tears were originally treated by removing the meniscus in an operation called a meniscectomy. However, results showed that removing the meniscus, either entirely or even partially, resulted in degenerative arthritis and instability in the knee.

As a result of the above-described complications, surgeons began treating torn meniscus tears with suturing techniques to retain as much of the meniscus as possible. However, suturing of a meniscal tear, like a meniscectomy, was originally an open technique, requiring a large incision and consequently longer periods of rehabilitation and recovery. Advances in instrumentation ultimately led to arthroscopic meniscal repair using long needles for passing suture through the tear.

More recently, various tacks and screws have been developed for meniscal repair, which can be used arthroscopically and simplify the surgery by eliminating the need for suturing altogether. See, for example, U.S. Pat. Nos. 4,873,976; 4,884,572; 4,895,148; 4,924,865; 4,976,715; 5,059,206; 5,129,906; 5,562,672; and 5,569,252. The known tacks and associated surgical methods have various disadvantages, such as the need for special preparation of the meniscus prior to insertion.

SUMMARY OF THE INVENTION

The present invention provides an improved meniscal repair device which, when used in conjunction with a specially-designed insertion gun, provides a simplified, quick and accurate method for repairing a torn meniscus.

Briefly, the meniscal repair device of the present invention has a pointed distal tip, a proximal end, and a cylindrical body provided with a plurality of crescent-shaped grooves. The grooves on the front end of device face proximally and are disposed on opposite sides of the device in alternating fashion. The grooves on the proximal end of the device face distally.

To insert the device into a torn meniscus, the device is first loaded into the elongated barrel of a spring loaded applicator, such that the back end of the device mates with the tip of the plunger of the applicator. The barrel of the applicator is then inserted through an incision in the knee and located arthroscopically at a location proximal and perpendicular to the tear in the meniscus. The trigger of the applicator is then actuated, releasing the plunger in the barrel, and driving the repair device distally into the meniscus across the tear. The distally facing grooves on the proximal end of the repair device limit forward motion of the device into the meniscus. Advantageously, the repair device of the present invention preferably is formed of a bioabsorbable material such as PLLA.

The device and method of the present invention can be used not only to repair meniscal tears as described herein, but can also be used to repair any bodily tissue, such as cartilage, bone, skin and ligaments.

Other features and advantages of the present invention will become apparent from the following description of the invention which refers to the accompanying drawings.

BRIEF DESCRIPTION OF THE DRAWINGS

FIG. 4 is a side view of the applicator used to insert the repair device in the method of the present invention.

FIG. 5 is a top view of the applicator used to insert the repair device in the method of the present invention.

FIG. 6 is a perspective view of the applicator used to insert the repair device in the method of the present invention.

DETAILED DESCRIPTION OF THE PREFERRED EMBODIMENTS

Figure 1:
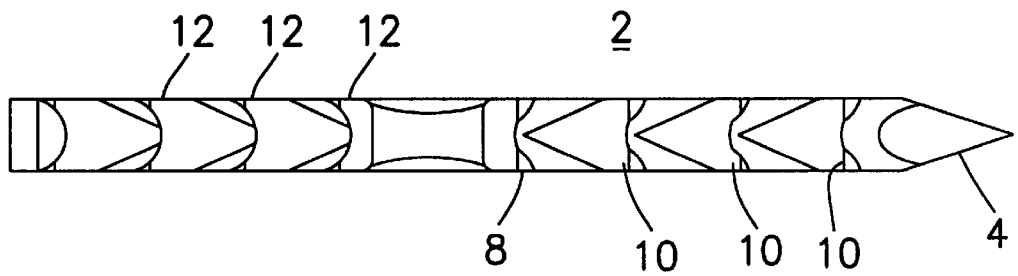
FIG. 1 is a side view of the repair device of the present invention.
Figure 2:
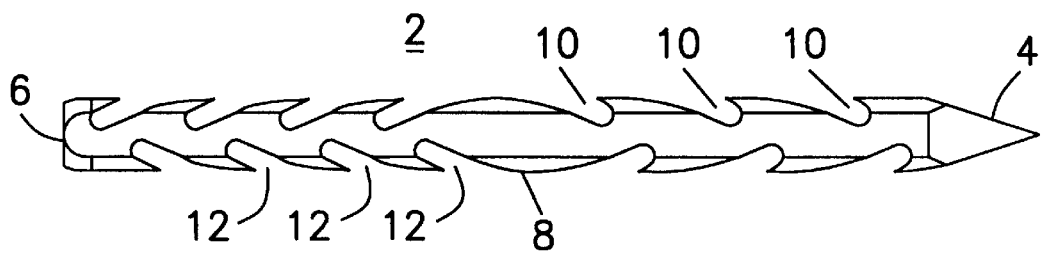
FIG. 2 is a top view of the repair device of the present invention.
Figure 3:
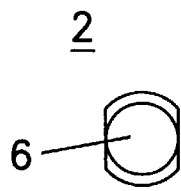
FIG. 3 is a proximal end view of the repair device of the present invention.

Referring first to FIGS. 1–3, the present invention comprises a meniscal repair device 2 which has a pointed trocar tip 4 on the distal end, a rounded proximal end 6, and a cylindrical body 8. Along the body 8 is a plurality of lateral, crescent-shaped grooves 10, 12, disposed on opposite sides of the device in alternating fashion.

The grooves are formed at an angle of about 30° to the axis of the body 8. Grooves 10 on the distal end of device 2 open proximally. Grooves 12 on the proximal end of the device open distally. The base of each groove typically is rounded. The surfaces of adjacent grooves 10, 12 on each side of the body 8 converge at an acute angle to form edges that anchor against the meniscal tissue.

The grooves are spaced equally at either end of the body 8, with the pattern of grooves on one side of the device being offset by about half the distance between grooves on the other side of the device.

The devices are provided in various lengths of 10 mm, 12 mm, and 14 mm. A device 2 of proper length is selected such that the inserted device does not protrude through the joint capsule.

To insert device 2 into a torn meniscus, the device is first loaded into the elongated barrel of a spring loaded applicator 14, shown in FIGS. 4–6. Applicator 14 has a structure similar in certain respects to that disclosed in U.S. Pat. No. 5,546,957, the entire disclosure of which is incorporated herein by reference. Applicator 14 has a spring-loaded plunger 16 that slides within a barrel 18. After the plunger of applicator 14 has been retracted by pulling rearwardly on knob 20, repair device 2 is loaded, proximal end first into applicator 14, such that proximal end 6 of device 2 mates with the tip of plunger 16 of applicator 14.

After applicator 14 has been loaded with a repair device 2, applicator 14 is grasped by a handle 22 and inserted through an incision in the knee, and the tip 23 of barrel 18 is located arthroscopically at a location proximal and perpendicular to the tear in the meniscus. After a safety on the applicator 14 has been switched off, trigger 26 of the applicator is actuated by the surgeon, releasing plunger 16 to move forcefully forwardly in barrel 18 under the force of spring 28, driving the repair device out of barrel 18 and distally into the meniscus across the tear. Protruding portions of the repair device can be cut off, through small separate incisions, if necessary. Advantageously, the repair device of the present invention is preferably formed of a bioabsorbable material such as PLLA.

Figure 7:
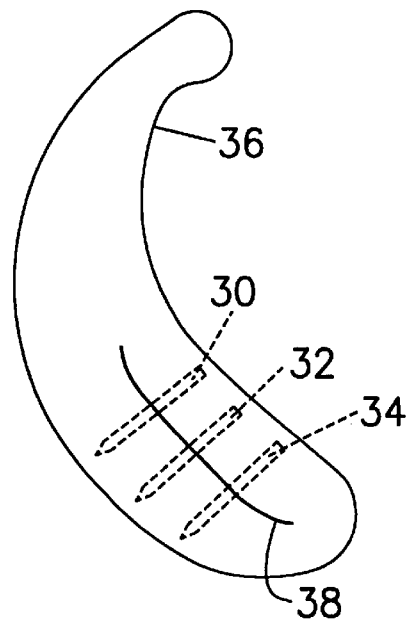
FIG. 7 is a schematic representation of a tissue repair using the repair device of the present invention.

Referring to FIG. 7, three repair devices 30, 32, and 34 according to the present invention are shown having been inserted into tissue 36 to approximate a tear 38. The proximally-facing grooves of the repair devices limit the rearward motion. The distally-facing grooves limit the forward motion of the devices, and prevent over-insertion.

The device and method of the present invention can be used not only to repair meniscal tears as described herein, but can also be used to repair any bodily tissue, such as cartilage, bone, skin and ligaments.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A tissue repair device comprising an elongate body having a pointed distal tip, a proximal end, opposing sides, a central axis, and a plurality of lateral grooves disposed along each of the opposing sides of the body, the grooves forming a regular pattern, the pattern on one side of the elongate body being offset from the pattern on the opposite side of the body, the grooves having a crescent shape, wherein grooves disposed near the distal tip of the device are angled to open proximally and grooves disposed near the proximal end are angled to open distally, and wherein surfaces of adjacent grooves converge at an acute angle to form sharp edges for anchoring against tissue, the body being configured for the repair of tissue.

2. The tissue repair device of claim 1, wherein the elongate body has opposing sides, and the grooves are disposed on opposite sides of the body.

3. The tissue repair device of claim 2, wherein the grooves form a regular pattern, the pattern on one side of the elongate body being offset from the pattern on the opposite side of the body.

4. The tissue repair device of claim 1, wherein the number of grooves disposed near the distal tip of the device is less than the number of grooves disposed near the proximal end.

5. The tissue repair device of claim 1, wherein the grooves are formed at an angle of about 30 ° with respect to the central axis.

* * * * *